United States Patent [19]

Krause

[11] Patent Number: 4,787,375

[45] Date of Patent: Nov. 29, 1988

[54] THERAPEUTIC APPARATUS

[76] Inventor: Nicolaas J. P. R. Krause, P.O. Box 3386, Kenmare, Krugersdorp, 1745, South Africa

[21] Appl. No.: 881,248

[22] Filed: Jul. 2, 1986

[30] Foreign Application Priority Data

Jul. 2, 1985 [ZA] South Africa .................. 85/4992

[51] Int. Cl.$^4$ ................................. A61F 5/00
[52] U.S. Cl. ................................. 128/70; 272/144; 297/326; 128/24 R
[58] Field of Search ............ 128/25 R, 24 R, 70, 128/74, 68, 71, 93; 272/144, 134; 297/142, 258, 260, DIG. 7, 326, 325, 311, 312, 337, 353, 473, 383, 487, 488, 483, 484; 248/371, 397

[56] References Cited

U.S. PATENT DOCUMENTS

| 1,938,435 | 12/1933 | MacAllister | 297/326 |
|---|---|---|---|
| 2,446,275 | 8/1948 | Glasin | 272/144 X |
| 2,726,712 | 12/1955 | Weller | 297/337 |
| 3,298,685 | 1/1967 | Williams | 272/144 X |
| 3,463,145 | 8/1969 | Whitaker . | |
| 3,568,669 | 3/1971 | Stites . | |
| 3,722,507 | 3/1973 | Krause . | |
| 3,752,153 | 8/1973 | Copeland | 128/70 X |
| 3,794,023 | 2/1974 | Bradley | 128/24 R X |
| 3,837,704 | 9/1974 | Bauer | 297/353 X |
| 3,899,042 | 8/1975 | Bonar | 297/487 |
| 4,170,988 | 10/1979 | Krause . | |
| 4,214,790 | 7/1980 | Sieber | 272/144 X |
| 4,248,480 | 2/1981 | Kovcky et al. | 297/473 |
| 4,292,962 | 10/1981 | Krause . | |
| 4,482,120 | 11/1984 | Fudala | 297/325 X |
| 4,595,234 | 6/1986 | Kjersem | 297/270 X |
| 4,632,458 | 12/1986 | Brown et al. | 297/353 |
| 4,638,793 | 1/1987 | Therkorn | 128/71 |
| 4,688,557 | 8/1987 | Bradstreet | 128/71 |

FOREIGN PATENT DOCUMENTS

| 445629 | 11/1912 | France | 272/134 |
|---|---|---|---|
| 2141623 | 1/1985 | United Kingdom | 297/337 |

OTHER PUBLICATIONS

Atlantic Fitness Products; 272/93; 11/1/85; p. 35.

Primary Examiner—Richard J. Apley
Assistant Examiner—Howard Flaxman
Attorney, Agent, or Firm—Cushman, Darby & Cushman

[57] ABSTRACT

A therapeutic apparatus for assisting the movement of the contents of the tubular systems of the human body includes a support frame, a cradle rotatably mounted on the support frame, a seat mounted on the cradle to be movably adjustable relative to the cradle, a counterbalance adjustably secured to the cradle for adjusting the centre of gravity of the apparatus before use, and securing structure mounted on the seat to secure a user in position on the seat at or near the user's groin.

3 Claims, 5 Drawing Sheets

THERAPEUTIC APPARATUS

BACKGROUND OF THE INVENTION

This invention relates to a therapeutic apparatus for assisting the movement of the contents of the tubular systems of the human body.

The Applicant is aware that certain individuals, more particularly bed-ridden patients, experience difficulty with the movement of the contents of the tubular systems of their bodies, such as the circulation of blood, particularly to reach the extremities of the limbs, the circulation of lymph in the lymphatic vessels, the movement of alimentary matter in the alimentary canal and the movement of excretory matter in the excretory system.

The Applicant believes that regular use of the apparatus of the invention contributes towards preventing the accumulation of blood in the extremities of the human body as well as stimulating movement of the contents of other tubular systems of the human body namely the air tubes, the lymphatic vessels and the alimentary canal, thereby also contributing towards a more even distribution of blood and nutrients in the body, and consequently towards more blood and threfore oxygen reaching the brain. Application believes that the circulatory function of the heart is thereby also assisted.

Applicant believes that this is achieved by using the apparatus of the invention to vary or alternate at a desired rate the orientation of the human body in relation to the constant direction of application of gravitational force to assist the circulatory, alimentary, excretory and other functions of the human body dependent upon or assisted by gravity for their effective functioning.

SUMMARY OF THE INVENTION

According to the invention, there is provided a therapeutic apparatus for assisting the movement of the contents of the tubular systems of the human body which includes:
 a support frame;
 a cradle rotatably mounted on the support frame;
 a seat mounted on the cradle to be movably adjustable relative to the cradle;
 a counterbalance adjustably secured to the cradle for adjusting the centre of gravity of the seat and cradle of the apparatus before use; and
 securing means mounted on the seat to secure a user in position on the seat at or near the user's groin region.

The support frame may include two uprights having pedestals, the uprights being held in laterally spaced relationship by a connecting crosspiece.

In one embodiment of the invention, the cradle may be in the form of a square U-shaped bracket mounted to be rotatable in a substantially vertical plane on the support frame so that the plane of rotation of the cradle coincides with the sagittal plane of the user. The sagittal plane is the median vertical longitudinal plane of the human body.

The cradle may be movably adjustable relative to the rotatable mounting by means of telescoping arms provided on the limbs of the bracket.

The cradle may be rotatably mounted on the support frame by means of stub axles provided on the telescoping arms co-operating with complementary slots provided on the uprights of the support frame.

In the embodiment of the invention under discussion, the seat may include a backrest and may be movably adjustable relative to the cradle by means of a telescoping arm provided in the backrest of the seat.

The backrest of the seat is inclined at an acute angle, preferably approximately 75°, to the horizontal axis of the seat.

The counterbalance may include one or more cast-iron masses secured to one of the telescoping arms to that the mass or masses are in a forward position relative to the seat.

The securing means may include an anchoring flap adjustably mounted on the seat to be locatable on the lap of a user of the apparatus at or near the groin of the user.

The anchoring flap may be slidably mounted on the seat and horizontally adjustable by means of ratchet mechanisms mounted on the seat co-operating with the slidably mounted flap.

Further securing means may be provided in the form of a chest plate locatable against the chest of a user to further secure the user in position on the seat. The chest plate may be pivotally mounted on the seat to be locatable against the chest of a user of the apparatus.

In another embodiment of the invention, the cradle may be an open framework mounted to be rotatable in a substantially vertical plane on the support frame, so that the plane of rotation of the cradle intersects the sagittal plane of the user.

The cradle may be rotatably mounted on the support frame by means of stub axles provided on the cradle co-operating with complementary slots provided on the uprights of the support framework.

A drive wheel may be drivingly connected to one of the stub axles of the cradle. The drive wheel may be driven off a motor, e.g. an electric motor.

The seat may include a support framework adjustably mounted on the cradle, and a seating surface mounted within the support framework.

The seating surface may be inclined at an acute angle to the horizontal axis of the seat.

The counter balance may include one or more cast-iron masses adjustably mounted at one end of the cradle.

The seat may be movably adjustable relative to the cradle by means of a screw jack mounted on the cradle.

The securing means may include thigh pads adjustably mountable to the seat to secure a user's thighs to the seat at or near the user's groin region.

In this embodiment of the invention the seat may include support means for supporting the lower legs, arms and head of the user.

BRIEF DESCRIPTION OF THE DRAWINGS

The invention will now be described by way of example, with reference to the accompanying diagrammatic drawings.

In the drawings.

DESCRIPTION OF THE EMBODIMENTS

Figure 1:
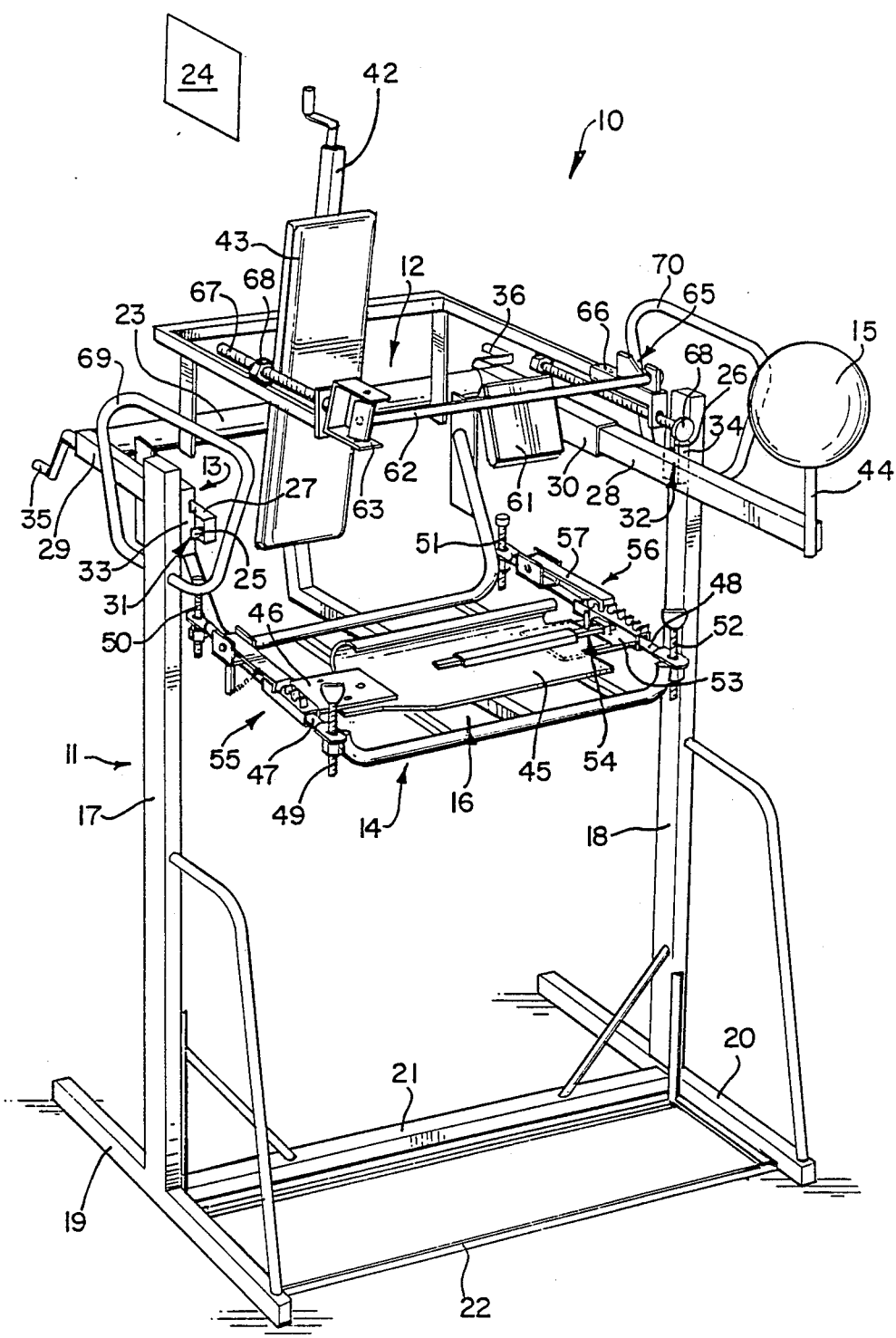
FIG. 1 shows a three-dimensional view of one embodiment of a therapeutic apparatus of the invention.

In the drawings, reference numeral 10 indicates generally a therapeutic apparatus for assisting the movement of the contents of the tubular systems of the human body according to the invention.

Referring to FIG. 1 of the drawings, the apparatus 10 includes a support frame 11, a cradle 12 rotatably mounted by means of a rotatable mounting 13 on the support frame 11 and movably adjustable relative to the rotatable mounting 13. It further includes a seat 14 secured to the cradle 12 and movably adjustable relative to the cradle 12. A counterbalance 15 is secured to the cradle 12 for adjusting the centre of gravity of the seat 14 before use. Securing means 16 are mounted on the seat 14 to secure a user in position on the seat 14 at or near the user's groin region, and adapted to support the user in an inverted position in the seat 14.

The support frame 11 includes two upright posts 17 and 18 having pedestals 19 and 20 and being held in laterally spaced relationship by a connecting crosspiece 21. The support frame is strengthened by abracing member 22 extending between the upright posts 17 and 18.

The cradle 12 is in the form of a square U-shaped bracket 23 mounted to be rotatable in a substantially vertical plane 24, coinciding with the sagittal plane of a user, on the support frame 11 by means of stub axles 25 and 26 provided on telescoping arms 27 and 28 which telescope into and out from the free ends of the limbs 29 and 30 of the bracket 23. The stub axles 25 and 26 slide into complementary slots 31 and 32 provided on brackets 33 and 34 standing proud of the upright posts 17 and 18 of the support frame 11.

Figure 3:
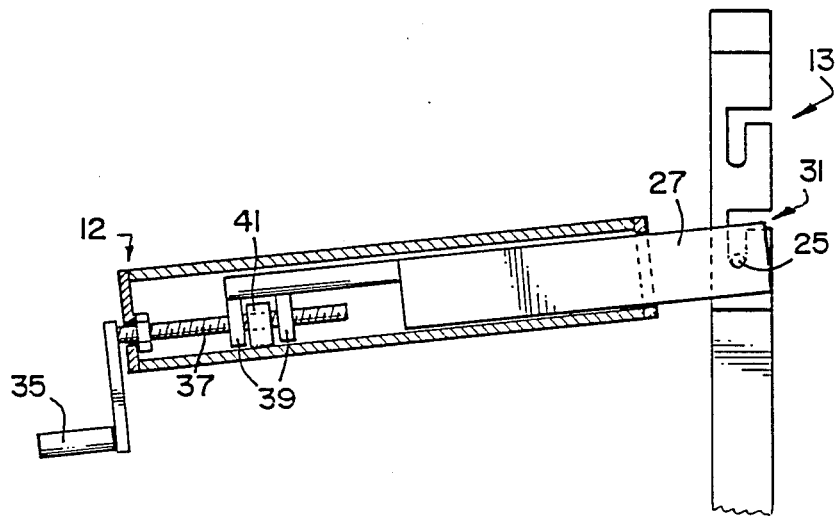
FIG. 3 shows a fragmentary part-sectional side view of one of the limbs of the cradle rotatably mounted on the support frame of the apparatus.

Referring to FIG. 3 of the drawings, the cradle 12 is movably adjustable relative to the rotatable mounting 13 by means of the telescoping arms 27 and 28 (28 shown in FIG. 1) which are provided in limbs 29 and 30 of the bracket 23. Telescoping arms 27 and 28 are operatively associated with limbs 29 and 30 by means of a cranks 35 and 36 (36 shown in FIG. 1) and screws 37 (only one shown) co-operating with complementary screw-threaded holes provided in lugs 39 (only one shown) provided on the arms 27 and 28, and a complementary screw-threaded nut 41 to telescope the arms 27 and 28 into and out from the free ends of the limbs 29 and 30 of the cradle 12.

Figure 2:
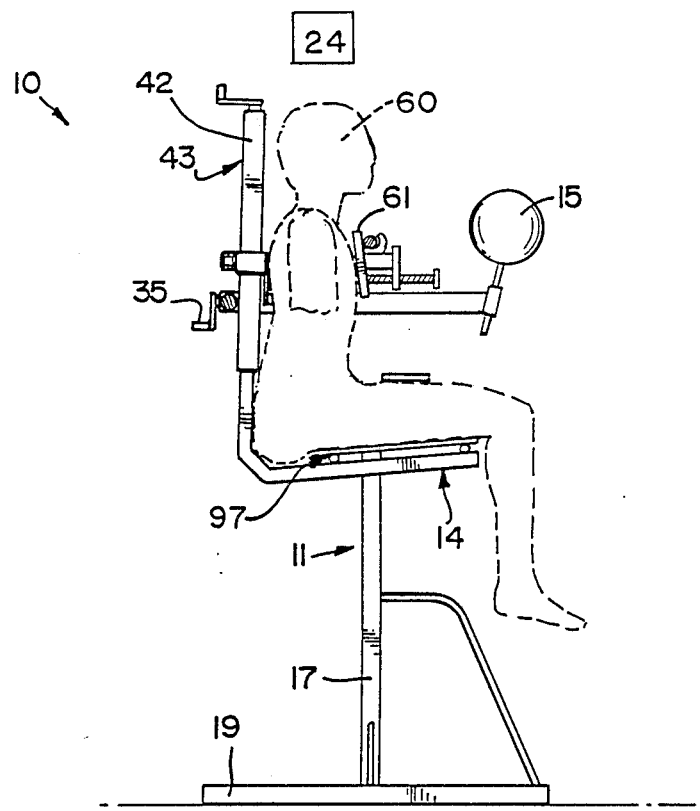
FIG. 2 shows a partly cut-away side view of the apparatus of FIG. 1.

Referring to FIGS. 1 and 2 of the drawings, the seat 14 is movably adjustable relative to the cradle 12 in a direction normal to the seat by means of a further telescoping arm 42 provided on the back-rest 43 of the seat 14.

The rear edge 97 of the seat 14 is spaced away from the backrest 43 to allow the buttocks of the user 60 to hook around the rear edge 97 of the seat 14.

The counterbalance 15 is in the form of a cast iron mass secured to telescoping arm 28 by means of rod 44, so that the counterbalance 15 is suspended in a forward position relative to the seat 14.

By operation of cranks 35 and 36, the centre of gravity of the seat 14 and cradle 11 is adjusted, and they are brought into balance before use of the apparatus 10 commences.

The securing means 16 includes an anchoring flap 45 secured to hinge member 46 which in turn is slidably mounted on one of rods 47 and 48 which rods are removably mounted on seat 14 by retaining bolts 49, 50, 51 and 52. The anchoring flap 45 is releasably securable to further hinge member 53 by means of a sliding bolt mechanism 54, and is adjustable by means of ratchet mechanisms 55 and 56 mounted on the seat 14 and co-operating with the slidably mounted flap 45.

Figure 4:
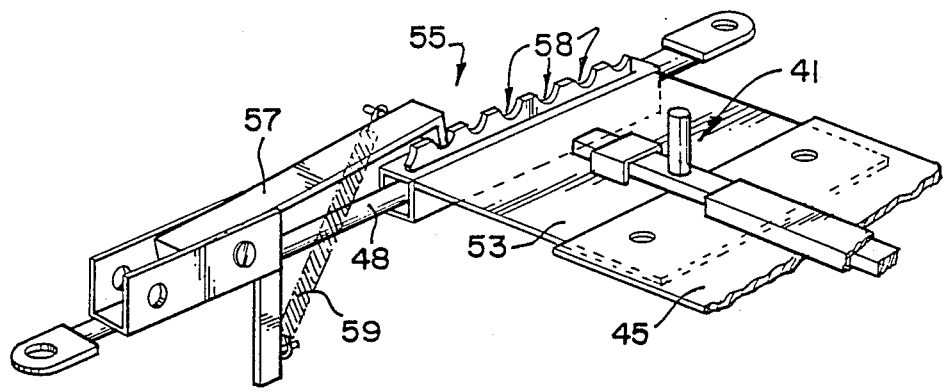
FIG. 4 shows a fragmentary three-dimensional view of an anchoring flap and ratchet mechanism of the apparatus according to the invention.

Referring to FIG. 4 of the drawings, the ratchet mechanism 55 shown includes a spring biassed engaging arm 57 engaging notches 58 provided on the hinge member 53 shown. The flap 45 is pivoted into a user's lap and locked in position by means of a slidable bolt mechanism 41 provided on the flap 45 releasably securing the flap 45 to hinge member 53. The flap 45 is then adjusted by sliding it backward or forward along rod 48 until it rests against the groin region of a user. The engaging arm 57 is then pivoted into position to engage notches 58 under bias of spring 59 and retain the flap 53 in position in the groin region of user 60 (FIG. 2).

Further securing means in the form of chest plate 61 is provided which is locatable against the chest of a user 60 to further secure the user 60 in position on the seat 14. The chest plate 61 is mounted on a pivotal arm 62 to be locatable against the chest of a user 60 of the apparatus 10. Pivotal arm 62 is pivotally mounted to bracket 63, which is in turn rotatably mounted on a support structure 64, itself mounted on cradle 12. The pivotal arm 62 engages slot 63 on sliding bracket 66 to retain the chest plate 61 in position against the chest of a user. The travel of bracket 63 and sliding bracket 66 relative to support structure 64 is adjustable by means of screw threaded shank 67 to which the bracket 63 is secured, co-operating with threaded nut 68, and screw stop 68 in operative engagement with sliding bracket 66, respectively, to fit chests of users of varying sizes.

In use, a user (60 in FIG. 2) pivots the arm 62 and flap 45 outwardly away from the seat 14 and seats himself on the seat 14. The inclination of the backrest 43 at approximately 75° to the horizontal axis of the seat 14 ensures that, when properly seated, the thighs of the user 60 are bent at an acute angle to the horizontal axis of the seat 14 for better fixation of the body in the apparatus 10. The user then pivots the arm 62 back so that chest plate 61 rests against his chest, and pivots the flap 45 back to rest on his lap and locks flap 45 in position by means of sliding bolt mechanism 54 securing flap 45 to hinge member 53. The user then slides the flap 45 horizontally backwards or forwards and locks it by means of the ratchet mechanism 56 in the desired position.

When securely seated in the apparatus 10, the user 60 may, by leaning forward, or by raising his arms above his head and then leaning forward, set himself and the apparatus 10 rotating. By alternately drawing his legs inward and pushing them outward, the user then maintains or speeds up the rotating motion. In order to stop himself and the apparatus 10 rotating, the user 60 may grasp handles 69 and 70 provided on uprights 70 and 18 as he approaches an upright seated position during rotation.

Figure 5:
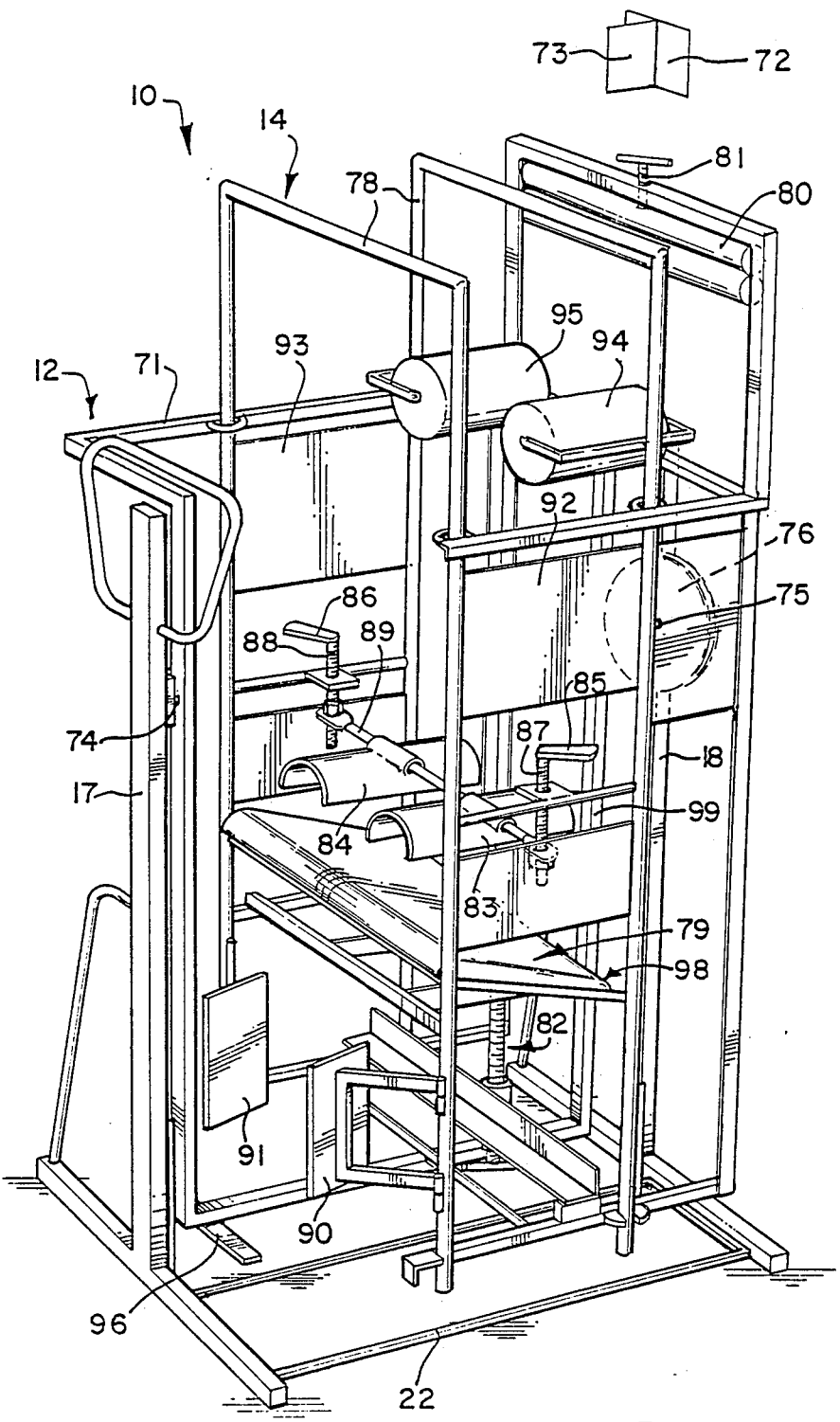
FIG. 5 shows a three-dimensional view of another embodiment of the therapeutic apparatus of the invention.
Figure 6:
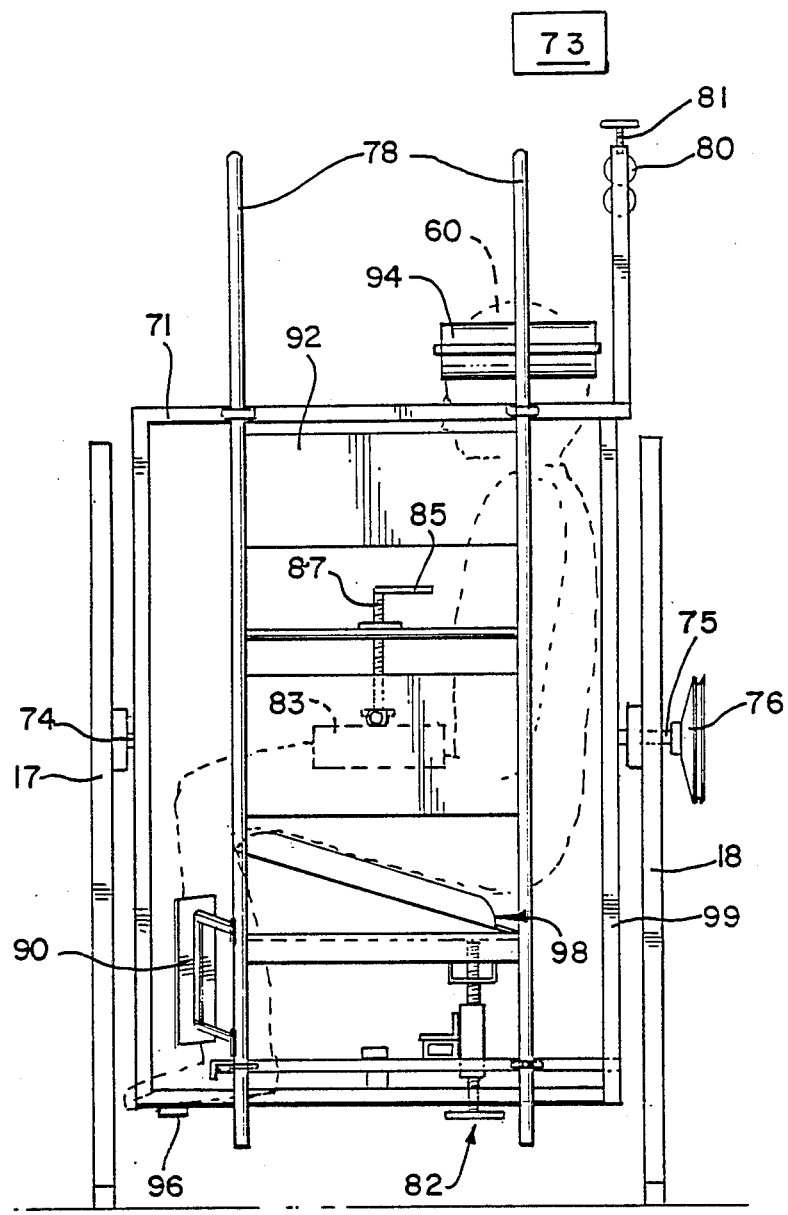
FIG. 6 shows a side view of the apparatus of FIG. 5.

Referring to FIGS. 5 and 6 of the drawings, in another embodiment of the invention, the user 60 of the apparatus 10, or patient, is in a completely passive situation where, Applicant believes, all his bodily functions as far as they are related to the movement of oxygen and nutritional material as well as excretory material can be taken over or at least assisted by an exterior force i.e.

centrifugal force which is applied to the body of the user or patient.

In this embodiment the cradle 12 is an open framework 71 mounted to be rotatable in a substantially vertical plane on the support frame 11, so that the plane of rotation 72 the framework 71 intersects the sagittal plane 73 of the user 60. The open framework 71 is rotatably mounted on the support frame 11 by means of stub axles 74 and 75 provided on the framework 71 co-operating with the complementary slots 31 and 32 provided on the uprights 17 and 18 of the support framework 11.

A drive wheel in the form of a pulley 76 is drivingly connected to one of the stub axles 75. The pulley 76 may be driven off an electric motor (not shown) thereby to rotate the framework 71 of the apparatus 10 in use.

The apparatus 10 has a seat 14 which includes a support framework 78 adjustably mounted on the open framework 71, and a seating surface 79 mounted within the support framework 78. The seating surface 79 is inclined at an acute angle to the horizontal axis of the seat support framework 78. The rear edge 98 of the seating surface 79 is spaced away from the backrest 99 to allow the buttocks of a user to hook around the rear edge 98 of the seating surface 79.

The apparatus includes counterbalances in the form of cast iron bars 80 adjustably mounted by screw threaded shank 81 at one end of the open framework 71, to balance the cradle 12 and seat 14 with the user in horizontal position, before applying force to the pulley 76 to rotate the cradle 12 and seat 14.

The seat 14 is movably adjustable relative to the open framework 71 by means of screw jack 82 mounted on the open framework 71.

The securing means is in the form of thigh pads 83 and 84 adjustably mounted to seat 14 by means of cranks 85 and 86 and screws 87 and 88 co-operating with retaining yoke 89, to secure the thighs of a user 60 to the seat, on the seating surface 79 at or near the user's groin region.

The seat 14 includes support means for supporting the lower legs in the form of pivotally mounted lateral support plates 90 and 91, support means for supporting the arms in the form of fixed lateral support plates 92 and 93 mounted on the support framework 78 of the seat 14 and support means in the form of cushions 94 and 95 mounted on the support framework 78 of seat 14 to support the head of a user 60. The feet of a user 60 rest on footpiece 96 provided on the open framework 71.

In use, in the second embodiment of the invention, the user 60 is seated in the apparatus 10, and thigh pads 83 and 84 are fastened in place by means of cranks 85 and 86 respectively. The user's feet rest on footpiece 96, and the user's lower limbs are supported by pivoting lateral support plates 90 and 91 into position against the user's calves. User's head rests between cushions 94 and 95. The open framework 71 is then rotated until the user is in a horizontal position, and the centre of gravity of user 60, the seat 14 and cradle 12 is then adjusted by adjusting cast iron bars 80 by means of threaded shank 81, until the user 60, cradle 12 and seat 14 are in horizontal equilibrium. An exterior driving force is then applied to pulley 76 to set the user 60, cradle 12 and seat 14 rotating as desired.

I claim:

1. A therapeutic apparatus for assisting the movement of the contents of the tubular systems of the human body which includes:

a support frame;

a cradle in the form of a square U-shaped bracket mounted on the support frame to be rotatable in a substantially vertical plane on the support frame so that the plane of rotation of the cradle coincides with the sagittal plane of a user of the apparatus;

a seat mounted on the cradle to be movably adjustable relative to the cradle;

a counterbalance adjustably secured to the cradle for adjusting the centre of gravity of the seat and cradle of the apparatus before use; and securing means mounted on the seat to secure a user in position on the seat at or near the user's groin region, wherein the cradle is movably adjustable relative to the rotatable mounting by means of telescoping arms provided on the limbs of the bracket.

2. A therapeutic apparatus according to claim 1 wherein the seat includes a backrest and is movably adjustable relative to the cradle by means of a telescoping arm provided in the backrest, the backrest being inclined at an angle of approximately 75° to the horizontal axis of the seat;

a rear edge of the seat being spaced away from the backrest to allow the buttocks of a user to hook around the rear edge of the seat.

3. An apparatus as claimed in claim 1 wherein the cradle is rotatably mounted on the support frame by means of stub axles provided on the telescoping arms co-operating with complementary slots provided on the uprights of the support frame.

* * * * *